US012788212B2

(12) United States Patent
Levine et al.

(10) Patent No.: US 12,788,212 B2
(45) Date of Patent: Nov. 10, 2026

(54) ROBUST SURGICAL SCENE DEPTH ESTIMATION USING ENDOSCOPY

(71) Applicant: Covidien LP, Mansfield, MA (US)

(72) Inventors: Steven J. Levine, Framingham, MA (US); Meir Rosenberg, Newton, MA (US); Robert W. Pierce, Franklin, MA (US); Faisal I. Bashir, Andover, MA (US); David J. Hirvonen, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 240 days.

(21) Appl. No.: 18/282,270

(22) PCT Filed: Apr. 15, 2022

(86) PCT No.: PCT/US2022/024953
§ 371 (c)(1),
(2) Date: Sep. 15, 2023

(87) PCT Pub. No.: WO2022/221621
PCT Pub. Date: Oct. 20, 2022

(65) Prior Publication Data

US 2024/0156325 A1 May 16, 2024

Related U.S. Application Data

(60) Provisional application No. 63/175,285, filed on Apr. 15, 2021.

(51) Int. Cl.
*A61B 1/00* (2006.01)
*A61B 5/00* (2006.01)
(Continued)

(52) U.S. Cl.
CPC .. *A61B 1/000094* (2022.02); *A61B 1/000095* (2022.02); *A61B 1/000096* (2022.02);
(Continued)

(58) Field of Classification Search
None
See application file for complete search history.

(56) References Cited

U.S. PATENT DOCUMENTS 6,132,368 A 10/2000 Cooper
6,206,903 B1 3/2001 Ramans
(Continued)

FOREIGN PATENT DOCUMENTS

CN 111080778 A 4/2020
EP 3130273 A1 2/2017
(Continued)

OTHER PUBLICATIONS

Automatic Corrections of Human Body Depth Maps using Deep Neural Networks by Gojic et al. pub.: Serbian Journal of Electrical Engineering vol. 17, No. 3, Oct. 2020, 285-296 (Year: 2020).*
(Continued)

*Primary Examiner* — Keith M Raymond
*Assistant Examiner* — Michael S Kellogg
(74) *Attorney, Agent, or Firm* — Carter, DeLuca & Farrell, LLP

(57) ABSTRACT

A surgical robotic system includes an image processing device configured to receive a stereoscopic video feed and output a depth map. The image processing device may process the stereoscopic video feed through two different depth mapping algorithms concurrently and to compare the output of each of the algorithms (i.e., two depth maps) to determine whether the output of one of the algorithms is accurate.

8 Claims, 11 Drawing Sheets

(51) Int. Cl.
*A61B 34/30* (2016.01)
*A61B 1/04* (2006.01)
*A61B 34/20* (2016.01)

(52) U.S. Cl.
CPC ........ *A61B 1/00149* (2013.01); *A61B 5/6886* (2013.01); *A61B 34/30* (2016.02); *A61B 1/04* (2013.01); *A61B 2034/2055* (2016.02); *A61B 2034/2065* (2016.02)

(56) References Cited

U.S. PATENT DOCUMENTS 6,246,200 B1 6/2001 Blumenkranz et al.
6,312,435 B1 11/2001 Wallace et al.
6,331,181 B1 12/2001 Tierney et al.
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll et al.
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco et al.
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez et al.
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.

(56) References Cited

U.S. PATENT DOCUMENTS 8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart et al.
8,989,903 B2 3/2015 Weir et al.
9,002,518 B2 4/2015 Manzo et al.
9,014,856 B2 4/2015 Manzo et al.
9,016,540 B2 4/2015 Whitman et al.
9,019,345 B2 4/2015 O'Grady et al.
9,043,027 B2 5/2015 Durant et al.
9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti et al.
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,165 B2 10/2018 Power
10,092,344 B2 10/2018 Mohr et al.
10,123,844 B2 11/2018 Nowlin et al.
10,188,471 B2 1/2019 Brisson
10,198,872 B2 2/2019 Lurie et al.
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,755,428 B2 8/2020 Aswin
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.

(56) References Cited

U.S. PATENT DOCUMENTS

| | | | |
|---|---|---|---|
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 2019/0060013 | A1 | 2/2019 | McDowall et al. |

FOREIGN PATENT DOCUMENTS

| | | | | |
|---|---|---|---|---|
| EP | 3560413 A1 | | 10/2019 | |
| WO | WO-2020205829 A1 | * | 10/2020 | ............. G06V 10/44 |

OTHER PUBLICATIONS

Fast Depth Map Super-Resolution using Deep Neural Network by Korinevskaya et al. pub.: 2018 IEEE International Symposium on Mixed and Augmented Reality Adjunct pp. 117-122 DOI 10.1109/ISMAR-Adjunct.2018.00047 (Year: 2018).*

Virtual wall-based haptic-guided teleoperated surgical robotic system for single-port brain tumor removal surgery by Seung et al. pub.: Proceedings of the Institution of Mechanical Engineers, Part H: Journal of Engineering in Medicine vol. 231, Issue 1, Jan. 2017, pp. 3-19 (Year: 2017).*

Li, K., Pan, B., Gao, Wp. et al. Miniature 6-axis force/torque sensor for force feedback in robot-assisted minimally invasive surgery. J. Cent. South Univ. 22, 4566-4577 (2015). https://doi.org/10.1007/s11771-015-3007-7 (Year: 2015).*

International Search Report and Written Opinion of the International Searching Authority issued in corresponding application PCT/US2022/024953 mailed Aug. 3, 2022 (11 pages).

International Preliminary Report on Patentability issued in International Application No. PCT/US2022/024953 issued Oct. 12, 2023, 7 pages.

* cited by examiner

ROBUST SURGICAL SCENE DEPTH ESTIMATION USING ENDOSCOPY

CROSS REFERENCE TO RELATED APPLICATIONS

The present application is a U.S. National Stage Application filed under 35 U.S.C. § 371(a) of International Patent Application No. PCT/US2022/024953, filed on Apr. 15, 2022, which claims the benefit of and priority to U.S. Provisional Application No. 63/175,285, filed on Apr. 15, 2021. The entire disclosures of the foregoing applications are incorporated by reference herein.

BACKGROUND

Technical Field

The present disclosure generally relates to estimating dimensions (e.g., depth) in a video or image of a surgical site based on images captured by an endoscope. The endoscope may be used in a surgical robotic system having one or more modular arm carts each of which supports a robotic arm, and a surgical console for controlling the carts and their respective arms. The endoscope may be held by one of the robotic arms allowing for viewing of the surgical site.

Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

As minimally invasive surgery and surgical robotics advance, there is a strong desire to incorporate artificial intelligence and analytics into the surgical procedure to decrease risk and improve patient outcomes. This includes using artificial intelligence to analyze video data. Given video data from a stereoscopic endoscope, there are a number of existing techniques to generate a depth map or a 3D point cloud. However, there are benefits and drawbacks to each of the conventional techniques. Thus, there is a need to produce accurate depth maps.

SUMMARY

In many procedures including robot-assisted surgery, there is a strong demand to develop artificial intelligence capabilities that will assist the surgeon and improve patient outcomes. The terms "artificial intelligence," "data models," or "machine learning" may include, but are not limited to, neural networks, convolutional neural networks (CNN), recurrent neural networks (RNN), generative adversarial networks (GAN), Transformers, Bayesian Regression, Naive Bayes, nearest neighbors, least squares, means, and support vector regression, among other data science and artificial science techniques.

The present disclosure provides a method for generating a depth map or a 3D point cloud using recent analytical and deep learning-based algorithms operating on a stereoscopic endoscope video stream. Deep learning-based algorithms are capable of providing dense depth estimates (i.e., a depth value is associated with every pixel) and approximating depth even for feature-less regions of the image through context. However, these algorithms are more susceptible to errors due to inferring depth only from context as well as to training/test mismatch when the input is sufficiently different than training data. Some algorithms may also be harder to verify accuracy due to the black-box nature of many neural networks.

In various embodiments, the neural network may include a temporal convolutional network, with one or more fully connected layers, or a feed forward network. In various embodiments, training of the neural network may happen on a separate system, e.g., graphic processor unit ("GPU") workstations, high performing computer clusters, etc., and the trained algorithm would then be deployed on the video processing device.

Analytical, i.e., classical, reconstruction algorithms operate on optical principles, making the algorithms analyzable and trustworthy and not susceptible to training/test mismatch. Suitable analytical reconstruction algorithms include dense stereo reconstruction techniques and dense matching between two stereoscopic camera views to reconstruct the 3D scene. However, such algorithms may sometimes match features incorrectly due to the inherent local nature of these algorithms. Specifically, most of these classical algorithms only integrate information from limited local neighborhood and do not take the larger context into account. Some algorithms also fail to provide dense estimates and only provide estimates at certain pixels due to key points and features (i.e., sparse estimates). These algorithms also struggle in smooth feature-less regions of image. Some analytical reconstruction algorithms produce dense results by matching two stereoscopic camera views to reconstruct the 3D scene.

The present disclosure combines several depth-mapping techniques together, to produce a depth map that is more reliable than one produced from any single algorithm alone. The algorithm according to the present disclosure uses a calibrated stereoscopic endoscope. Initially, the left and right images are rectified. Next, an algorithm estimates the disparity (left-to-right difference at each pixel location). Two of the above-described algorithms were used: (1) an analytical approach that frames disparity as a global variational optimization, and (2) a machine learning-based approach that uses a convolutional neural network and loss function designed for 3D reconstruction. The disparity in pixels is then converted to a depth in meters via triangulation and is then converted to an equivalent 3D point cloud of the surgical scene. The resulting depth map may be used in plurality of applications that rely on a detailed 3D representation of the surgical scene. A non-exhaustive, representative enumeration of these applications includes: placing "virtual walls" around critical structures; automated instrument control, such as suturing; registering a pre-operative 3D model with intra-operative endoscopic video; fusing a separate imaging modality, for example, ultrasound, with endoscope video; creating, updating, and tracking a non-rigid SLAM model of the surgical scene to aid in situational awareness during surgery. A virtual wall acts as an movement limit beyond which the robotic arm and the instrument attached thereto. Thus, any inputs that would result in movement of the robotic arm and/or the instrument beyond the virtual wall are ignored.

Classical analytical reconstruction algorithms may be prone to inaccuracy and artifacts at locations with high depth discontinuities, yet they may provide reasonable bounds on plausible depth estimates when larger spatial windows or coarser process scales (i.e., lower resolutions) are considered.

When tested on novel "unfamiliar" scenes, which may be visually dissimilar to the training dataset, machine learning algorithms may fail to generalize well, resulting in disparity maps with multi-modal error distributions. In this case, one mode may correspond to typical or expected minor deviations from ground truth due to a combination of factors (e.g., uncompensated lens distortion, resolution limitations, feature ambiguity). Additional modes in the error distribution may correspond to gross disparity failures stemming from more consequential machine learning shortcomings (e.g., limitations in datasets, overfitting, etc.).

In scenes with favorable conditions (e.g., distinct textures, strong features, etc.) the deep learning algorithms may produce more accurate results on the whole. A heuristic fusion scheme could be crafted to exploit these complementary tendencies: accurate but less robust machine learning models paired with more robust but less accurate output from classical methods. In cases where there is agreement between classical and deep learning methods, preference may be given to deep learning disparity values. In cases where they disagree, the more robust disparity from the classical algorithm may be preferred. At strong depth discontinuities, where disagreement is expected, the deep learning values may be opportunistically selected if they are deemed plausible based on bounds established from the classical algorithm.

The present disclosure may also employ a fusion scheme providing additional smoothness constraint to avoid discontinuities resulting from the final hybrid disparity map. Furthermore, the fusion scheme may also be achieved through a machine learning process, where multiple complementary depth maps are considered as inputs to a deep learning model. These complementary depth maps may also be created by training multiple models on distinct complementary datasets.

According to one embodiment of the present disclosure, a surgical robotic system is disclosed. The surgical robotic system includes an endoscopic camera configured to output a stereoscopic video stream. The system also includes a video processing unit coupled to the endoscopic camera, the video processing unit configured to process the stereoscopic video stream using a first algorithm to obtain a first depth map. The video processing unit is also configured to process the stereoscopic video stream using a second algorithm to obtain a second depth map. The video processing unit is further configured compare the first depth map to the second depth map to determine accuracy of the first depth map.

Implementations of the above embodiment may include one or more of the following features. According to one aspect of the above embodiment, the first algorithm may be a deep learning image processing algorithm. The second algorithm may be an analytical reconstruction algorithm. The deep learning image processing algorithm may be adjusted based on the second depth map.

According to another embodiment of the present disclosure a method for processing video data of a surgical scene is disclosed. The method includes outputting a stereoscopic video stream from an endoscopic camera to a video processing unit; processing the stereoscopic video stream using a first algorithm to obtain a first depth map; processing the stereoscopic video stream using a second algorithm to obtain a second depth map; and comparing the first depth map to the second depth map to determine accuracy of the first depth map.

According to one aspect of the above embodiment, the method further includes generating a virtual wall based on the first depth map; and limiting movement of a robotic arm based on the virtual wall. The first algorithm may be a deep learning image processing algorithm. The second algorithm may be an analytical reconstruction algorithm. The method may further include adjusting the deep learning image processing algorithm based on the second depth map.

Processing the stereoscopic video stream using the second algorithm may further include receiving sensor feedback from at least one torque sensor corresponding to physical contact by a robotic instrument.

BRIEF DESCRIPTION OF THE DRAWINGS

Various embodiments of the present disclosure are described herein with reference to the drawings wherein.

DETAILED DESCRIPTION

Figure 1:
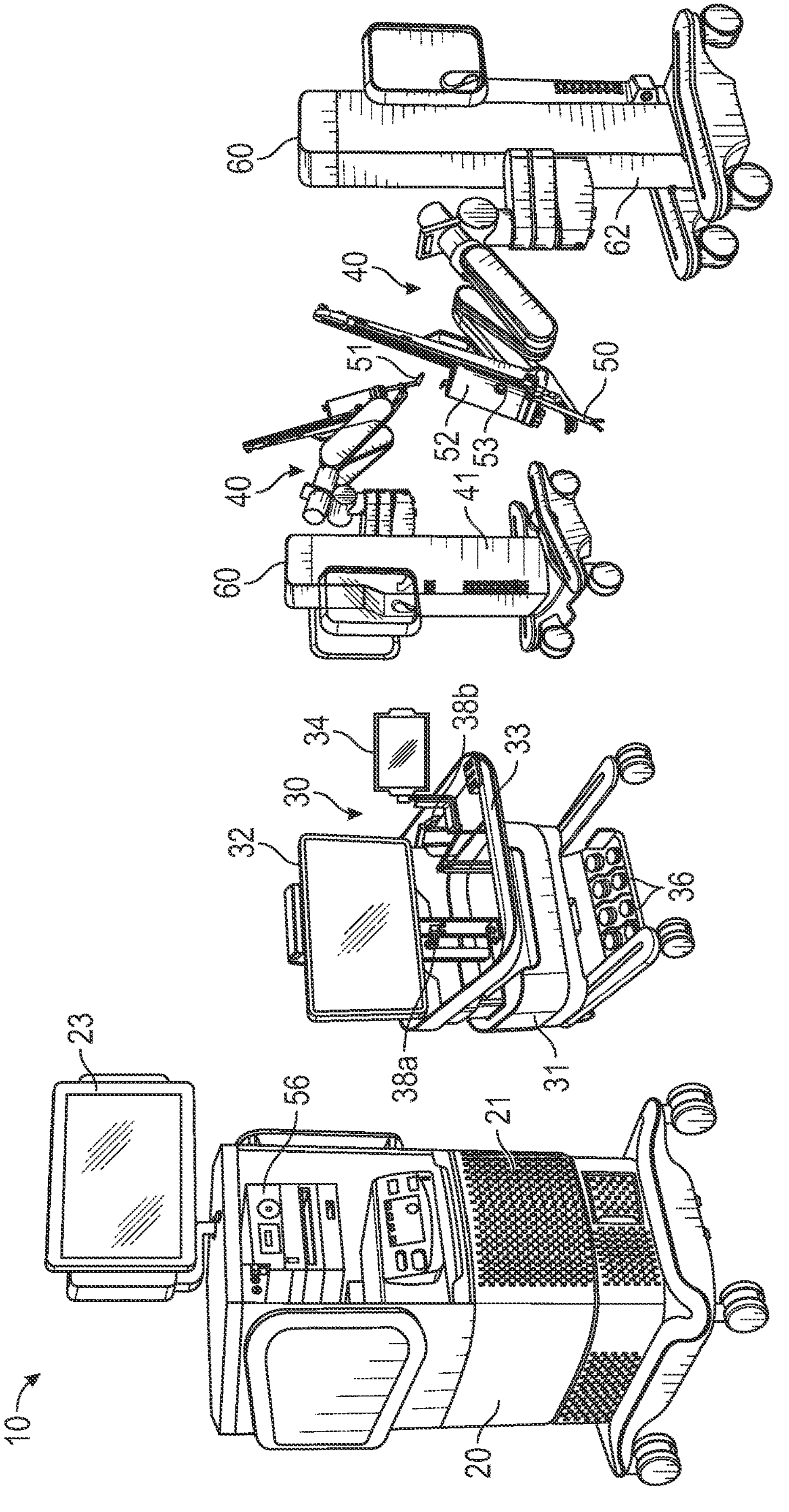
FIG. 1 is a schematic illustration of a surgical robotic system including a control tower, a console, and one or more surgical robotic arms according to an embodiment of the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the present disclosure and output the processed video stream.

The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38*a* and 38*b* which are used by a user to remotely control robotic arms 40. The surgical console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38*a* and 38*b*.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
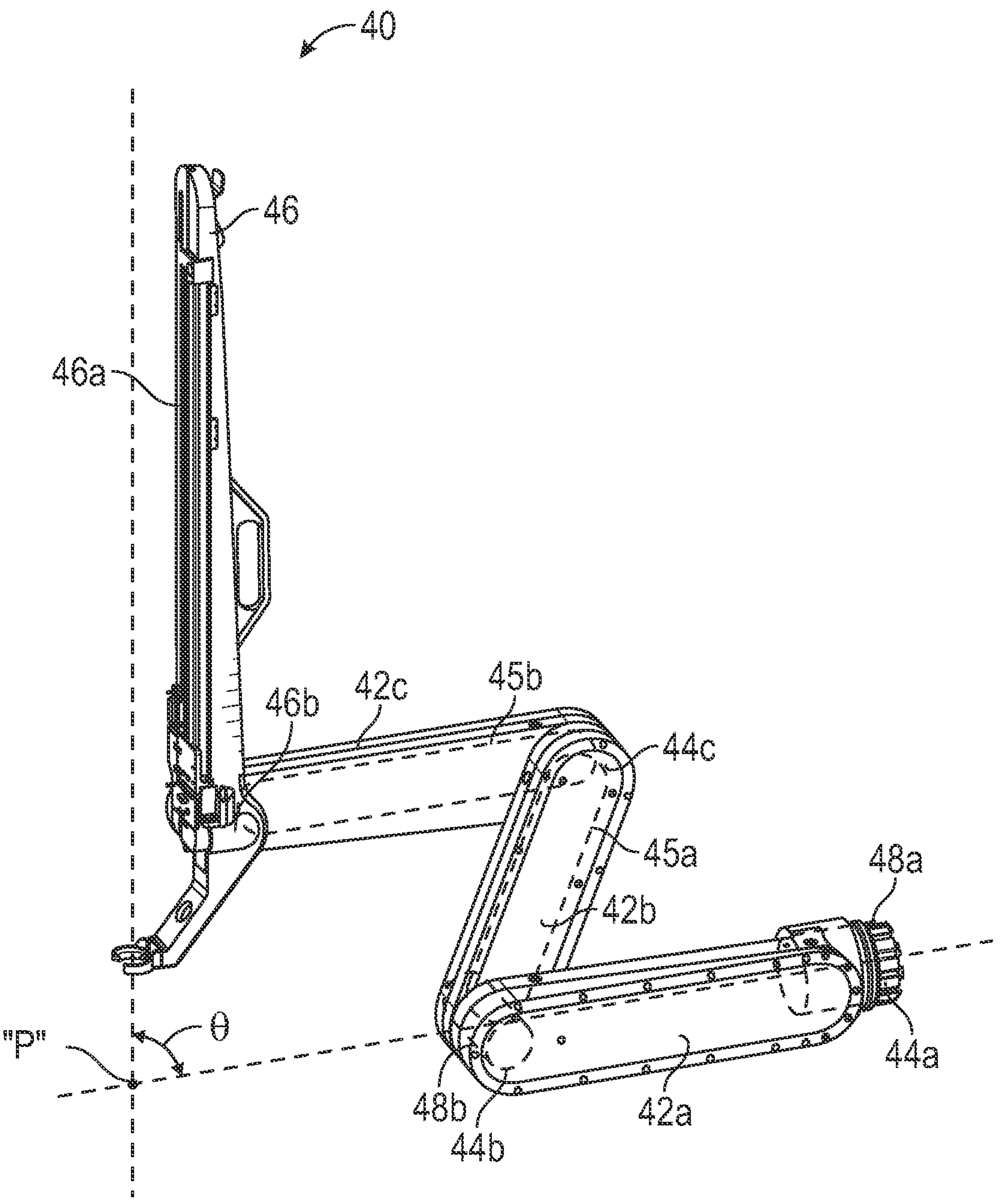
FIG. 2 is a perspective view of a surgical robotic arm of the surgical robotic system of FIG. 1 according to an embodiment of the present disclosure.
Figure 3:
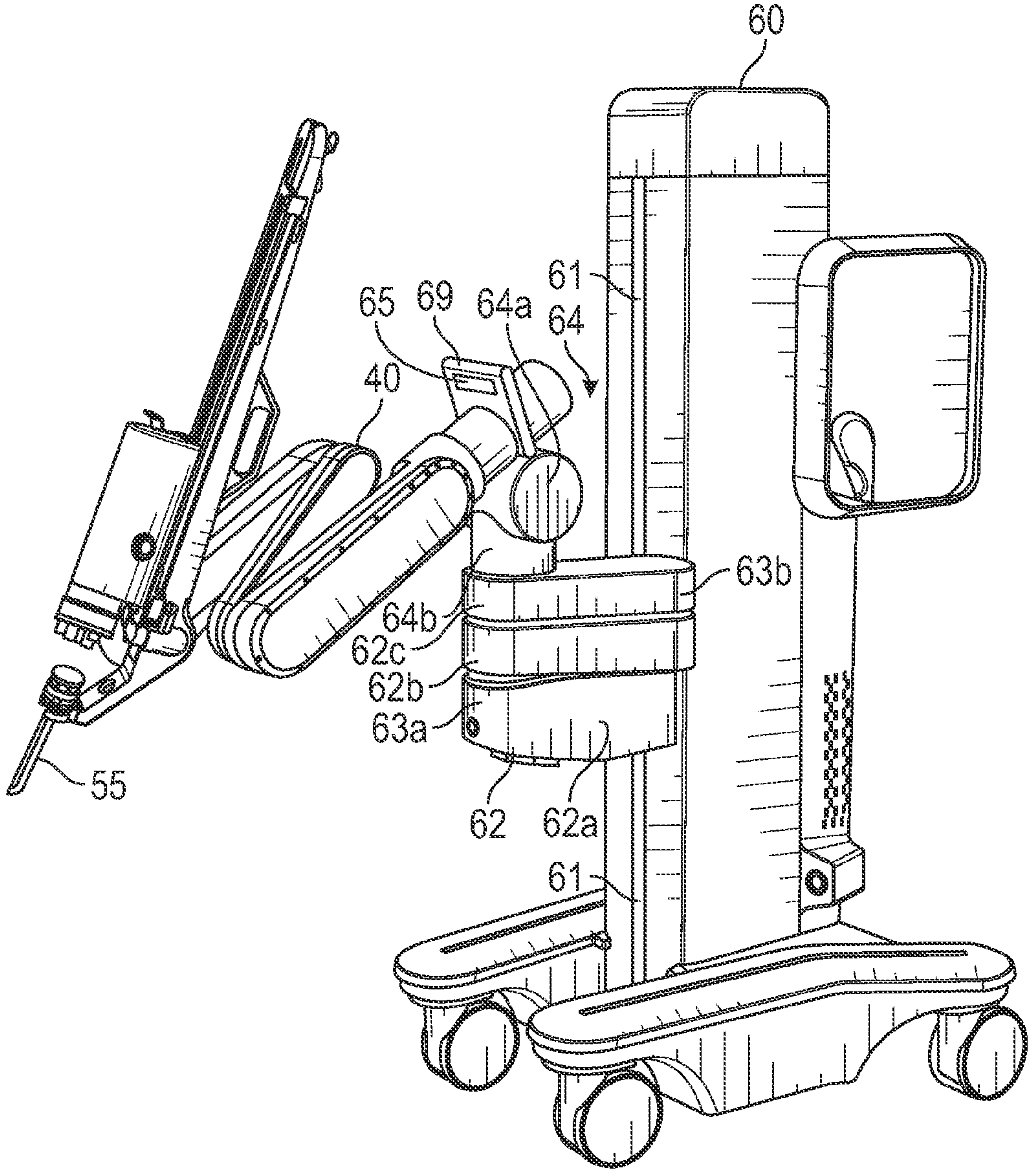
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
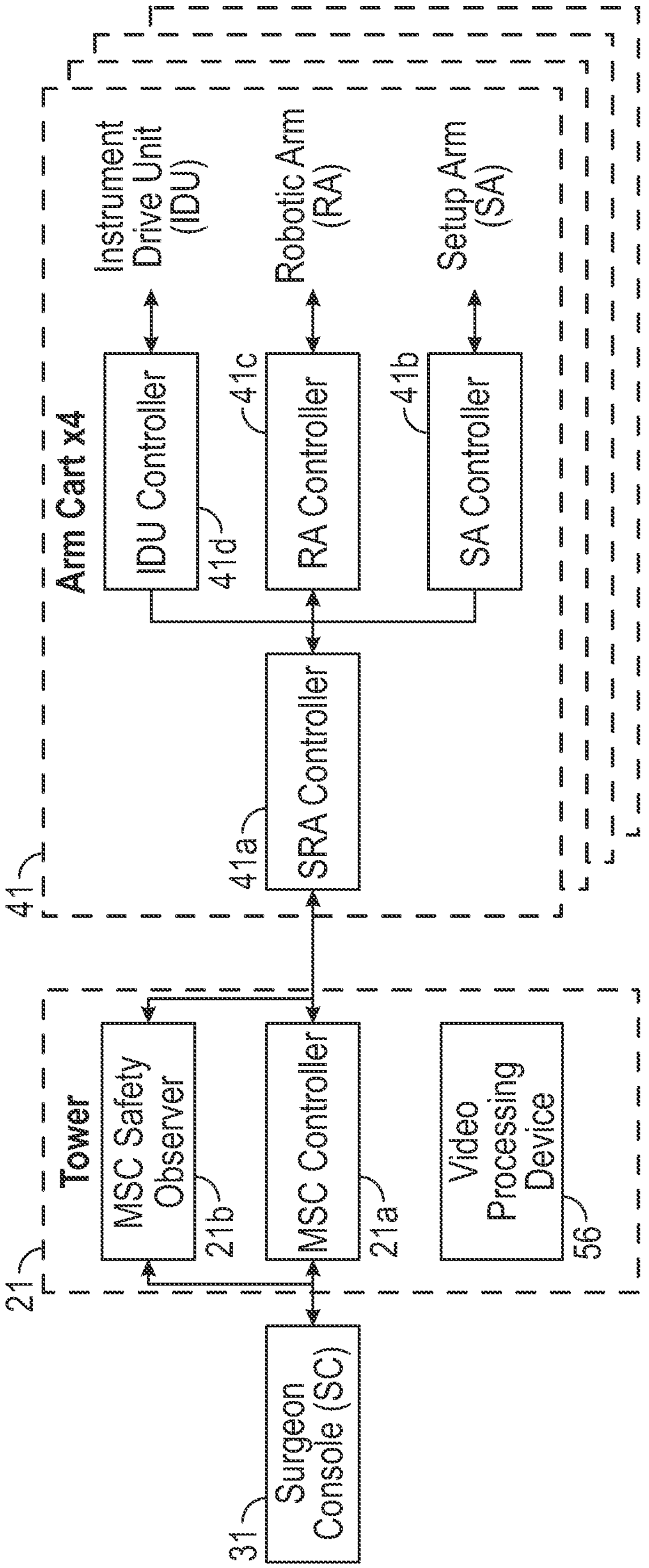
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgical console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgical console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

The setup arm controller 41*b* controls each of joints 63*a* and 63*b*, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38*a* is then scaled by a scaling function executed by the controller 21*a*. In embodiments, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
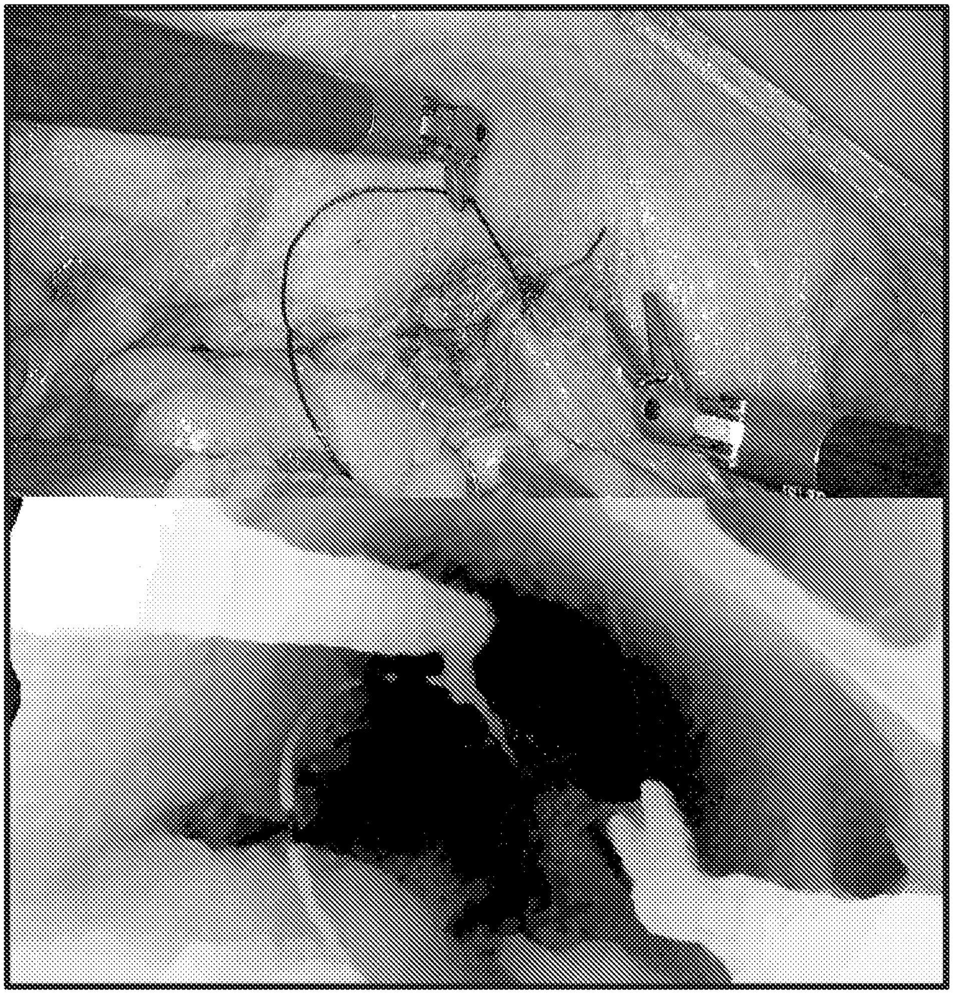
FIG. 5 is a black and white image from a stereoscopic endoscope (top) and a disparity map generated using an analytical reconstruction algorithm.
Figure 6:
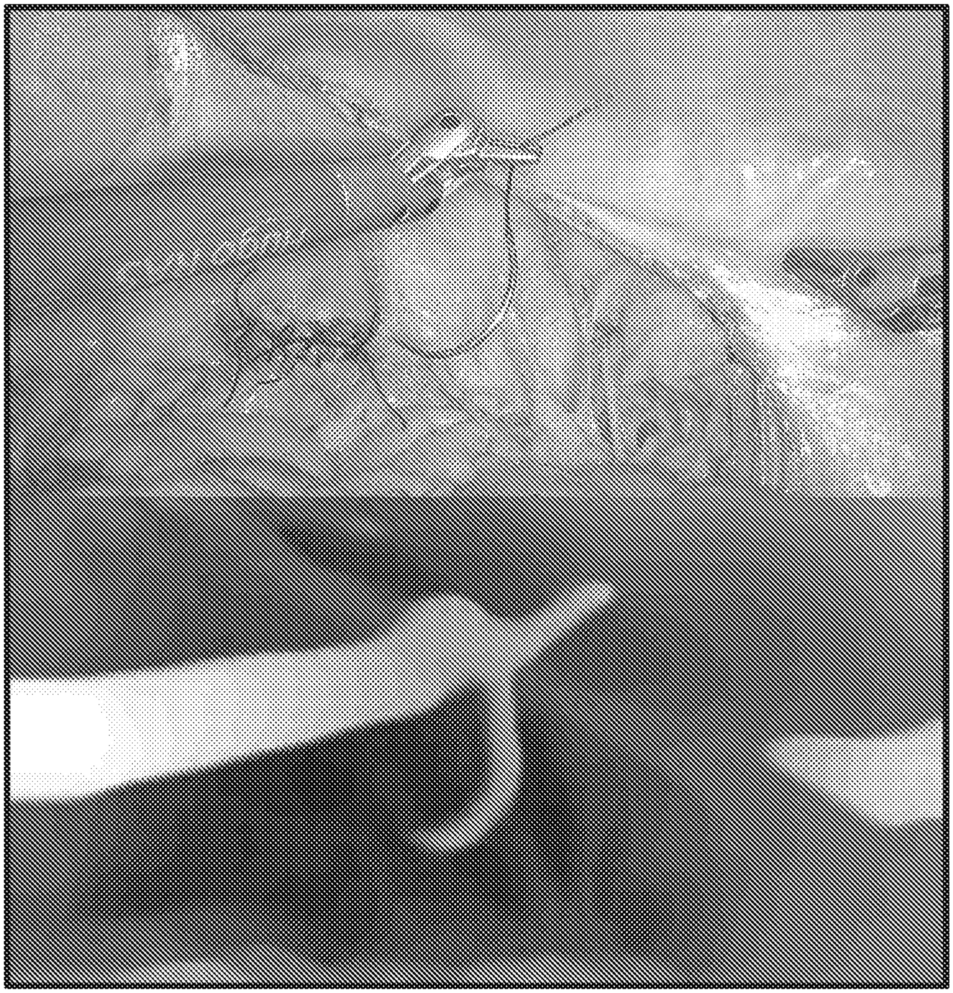
FIG. 6 is a color image from a stereoscopic endoscope (top) and a disparity map generated using a deep learning algorithm.
Figure 7:
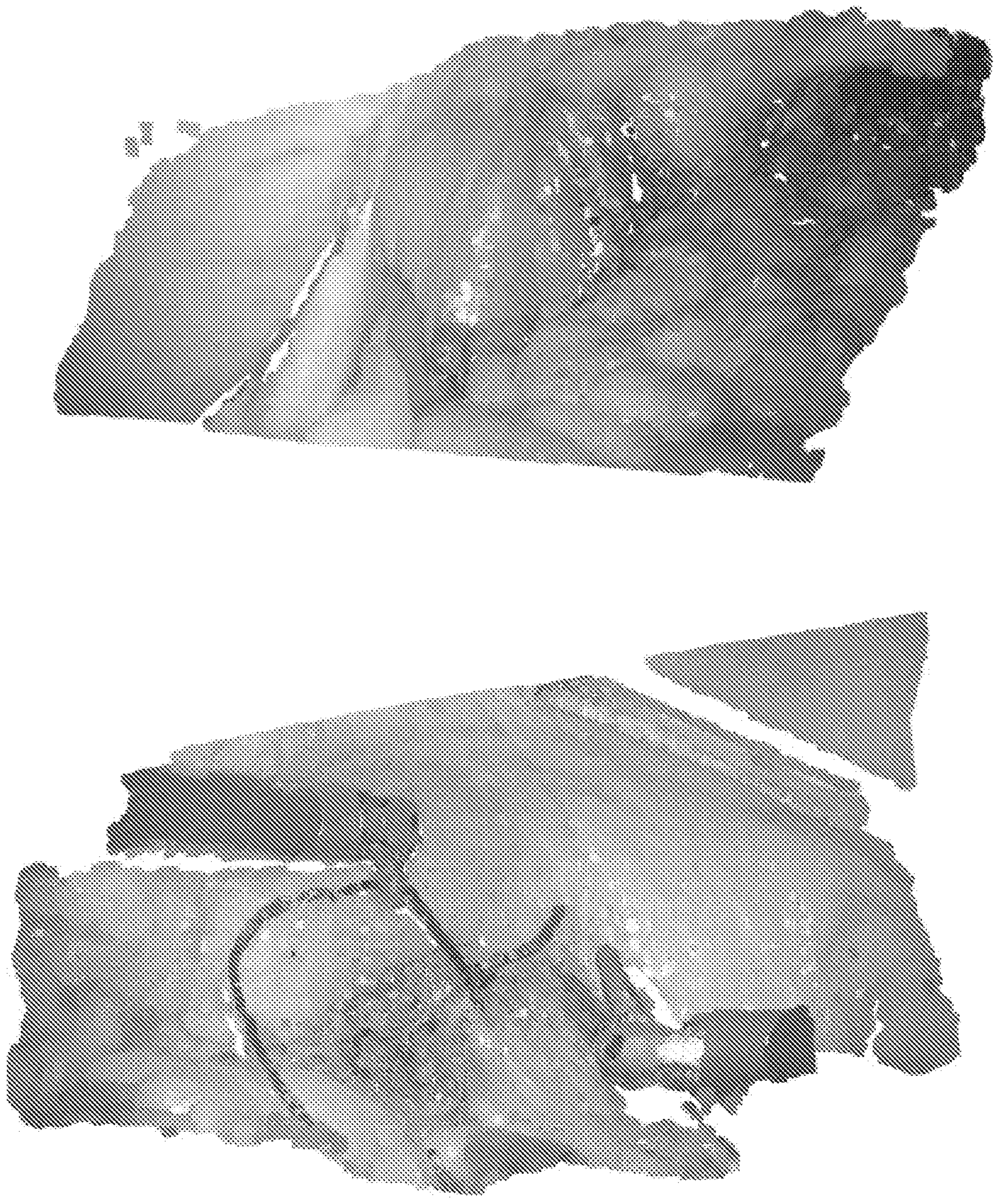
FIG. 7 is reconstructed point cloud from the depth map generated using the analytical reconstruction algorithm (top) and the depth map generated using the deep learning algorithm (bottom)

The video processing device 56 is configured to process the video feed from the endoscope camera 51 and to output a processed video stream on the first displays 32 of the surgical console 30 and/or the display 23 of the control tower 20. According to one embodiment, the video processing device 56 is configured to execute two image processing algorithms, namely an analytical reconstruction algorithm and a deep learning algorithm. In particular, the video processing device 56 uses an analytical reconstruction algorithm as a cross-check/validation of the deep learning algorithm. Both algorithms would be running in real time, processing the same endoscope images. The deep learning algorithm would produce a dense depth map as shown in FIG. 6, and the analytical reconstruction algorithm may produce only a sparse dense map for a subset of the points in image as shown in FIG. 5. The video processing device 56 then compares the corresponding depth values (dense versus deep learning) to see how closely they agree as shown in FIG. 7. If their difference exceeds a tolerance (either absolute or as a percentage) over a large fraction of key areas in the image, then the generated depth map may be deemed unreliable and unsuitable for use in other application (such as automated suturing). In this way, the video processing device 56 may use two (or possibly even more) independent implementations of depth mapping algorithms and check how well they agree with each other. After verifying that the first depth map is accurate, the depth map may then be used in various image enhancement algorithm, e.g., as an overlay, in the stereoscopic video stream.

According to another embodiment of the present disclosure, the video processing device 56, rather than validate the output of the deep learning algorithm, the video processing device 56 utilizes the data from the analytical reconstruction algorithm to correct in real-time the deep learning algorithm. If the deep learning and analytical reconstruction algorithm produce disagreeing depth estimates for certain key points, the dense deep learning algorithm output may be locally scaled, averaged, or spatially warped by adjusting its parameters to better match the analytical reconstruction algorithm, which may be more reliable for those key points. It may also be possible to incorporate "correction inputs" into the deep learning network itself to accommodate some of these corrections.

In further embodiments, other algorithms may be used to check depth map plausibility, to rule out strange or unexpected depth maps. A neural network could be trained for this purpose. Other simpler algorithms may also be used to detect sudden unexpected depth jumps in tissue-like regions that are expected to be smooth. Such algorithms could identify regions of anomalous depth maps to assess reliability.

According to yet another embodiment, the video processing device 56 may receive physical parameter data from the instrument 50, and the robotic arm 40 holding the instrument 50. In particular, robotic "touch", e.g., recorded as environmental torque by torque sensors of the robotic arm 40, may be used to refine or validate the depth map. The robotic arm 40 is calibrated to a known hand-eye matrix (i.e., the relationship between the 3D position of the robotic arm 40 and where the instrument 50 held by the robotic arm 40 appears on the screen is known). Thus, when instrument 50 is touching or grasping tissue or another object in the surgical scene, this contact is inferred via force or torque sensors. Touch may also be determined visually based on deformation of the tissue. Touch implies that the depth of the instrument tip is approximately equal to the depth of the surgical scene, allowing the position of the instrument 50, which is known from the robotic arm 40 torque sensors to be used as a proxy for depth in that location. These position estimates may be used as a cross-check or refinement for the optically-estimated depth.

The generated depth map may be combined with other 3D data such as various imaging scans (e.g., CAT scans, MRI, ultrasound, etc.). Such 3D data may be overlayed over the depth map and may be used to identify critical structures. The depth map may then be used by the computer 21 to generate virtual walls around critical structures, which would prevent movement of the instrument 50 beyond the virtual walls, thus limiting operating space of the robotic arms 40. In addition, the depth map may be used to adjust the color in the base color based on the change in angle from the depth map.

Depth mapping may also be used for estimation of axial distortion (e.g., image elongation/shrink in the depth direction). In conventional endoscopy, the aspect ratio of the objects being observed is unknown in the axial and transverse planes. Thus, depth mapping may be used to correct images in post-processing with respect to aspect ratios and other imaging distortions.

Figure 8:
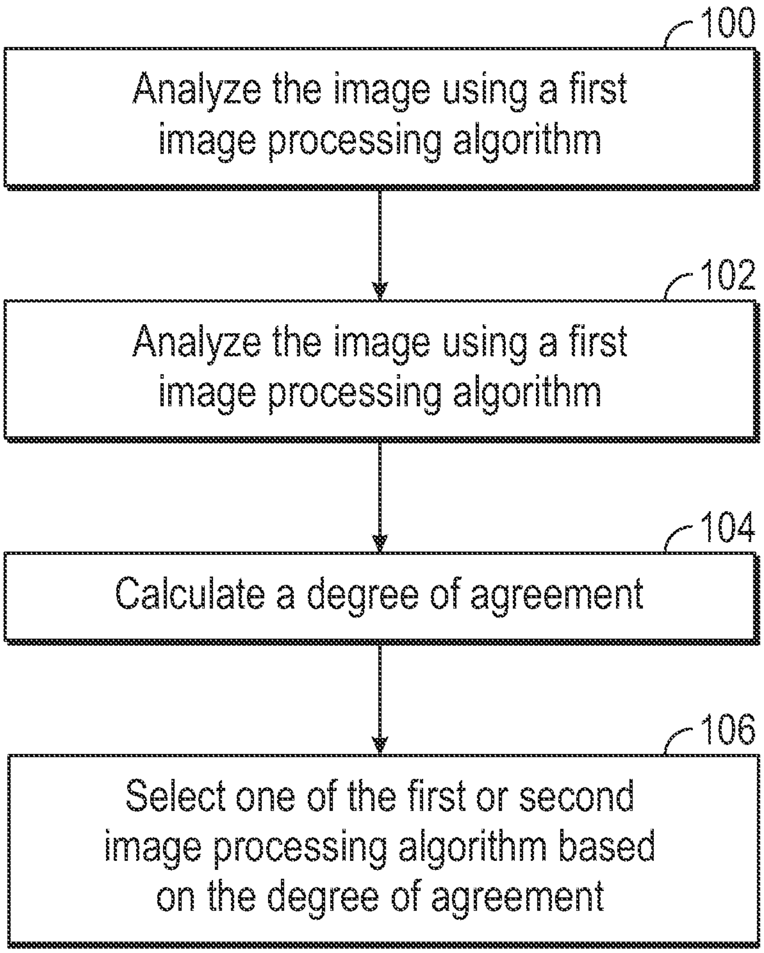
FIG. 8 is a flow chart of a method for generating a depth map according to an embodiment of the present disclosure.

With reference to FIG. 8, another method of utilizing complementary depth mapping algorithms in a fusion scheme. The method includes processing the image or video stream using a first image processing algorithm, e.g., analytical or classical, at step 100. At step 102, the image is then processing using a second image processing algorithm, e.g., machine learning algorithm. Thereafter, at step 104, a degree of agreement is calculated to determine which of the image processing algorithm should be given preference. At step 106, a preferred algorithm is selected, and the image is then processed based on the selected weighing of the algorithms.

In cases where there is agreement between classical and deep learning methods, preference is given to deep learning disparity values. In cases where the algorithms disagree, the more robust disparity from the classical algorithm is preferred. At strong depth discontinuities, where disagreement is expected, the deep learning values are selected if they are deemed plausible based on bounds established from the classical algorithm.

A fusion scheme method of FIG. 8 may employ some additional smoothness constraint to avoid additional discontinuities resulting from the final hybrid disparity map. Furthermore, the fusion scheme may also be achieved through a machine learning process, where multiple complementary depth maps are considered as inputs to a deep learning model. These complementary depth maps could also be created by training multiple models on distinct complementary datasets.

In further embodiments, multiple different networks—each optimized or trained to do well at estimating depth for certain things—some networks good at depth on tools, others good at depth for background tissue, some for smoke, etc. may be used. Heuristics (or even other neural networks) could be used to select which networks to use and how to "weigh" the outputs in generating a depth map.

The method of FIG. 8 may be modified to determine a degree of confidence in the depth map. In particular degree of agreement or disagreement as calculated in step 104 may be used to determine a degree of confidence, i.e., a high degree of disagreement denotes low degree of confidence. In response to determining that there is a low degree of confidence in the first algorithm, the video processing device 56 may trigger execution of the second algorithm. Alternatively, the degree of confidence may be used as a threshold to commence or prevent teleoperation of the system 10. Furthermore, teleoperations may be selectively activated based on the degree of confidence. Thus, certain features of the system 10 that rely on precise depth mapping, e.g., auto-suturing, may be disabled.

Confidence may also be used in blending of the surgical video from the endoscopic camera 51 and depth map. The resolution of depth map may degrade as the distance of the objects to the endoscopic camera 51 increases, therefore the blending of the video and depth map may be adjusted using a more weighted depth map at closer distances and less weighted depth map at further distances.

Figure 9:
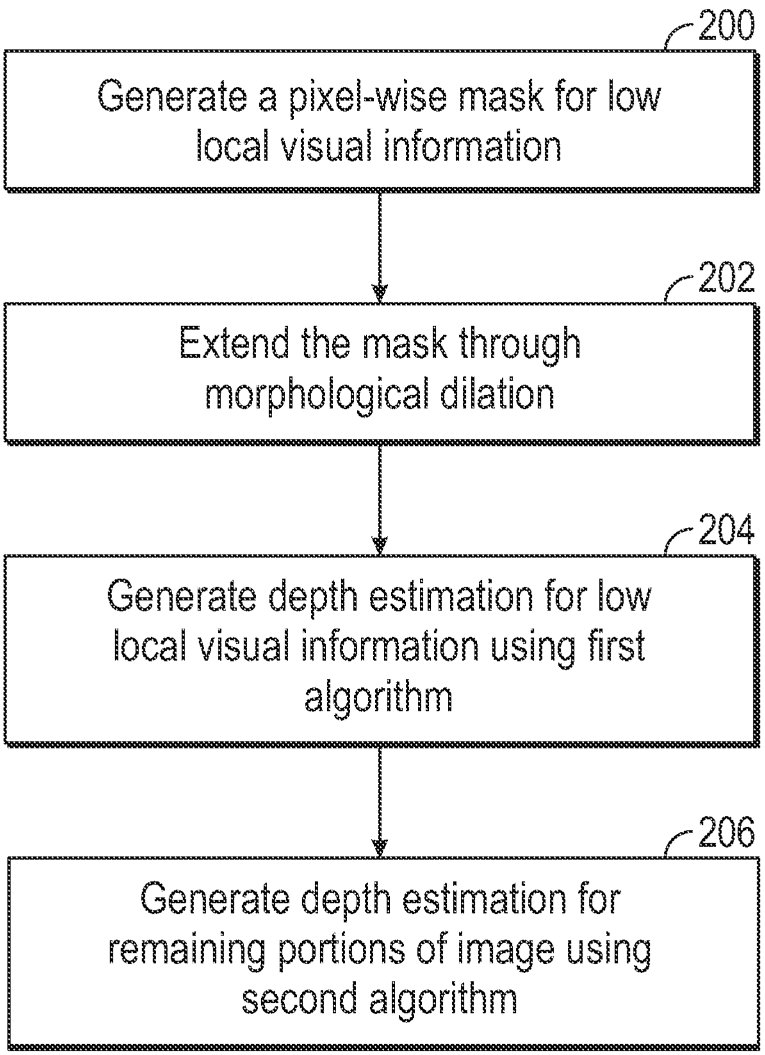
FIG. 9 is a flow chart of method of using complementary depth mapping algorithms according to an embodiment of the present disclosure.

With reference to FIG. 9, another method of using complementary depth mapping algorithms includes using a first image processing algorithm to fill in the values of the second algorithm and/or to remove inconsistent values thereby acting as an integrity check.

In the areas of low local visual information, the disparity may be more reliably measured by the first image processing algorithm, i.e., deep learning-based algorithm, that can integrate larger context. These areas of low visual information may be detected by local measures that compute the amount of high frequency content using a sliding window method. Examples of the phenomenon that generate areas of low visual information include shadows, specular reflection, smoke, etc.

During a typical surgical procedure, there are times when the surgical site exhibits long periods of smoke and blood in the images captured through stereo endoscope. When events such as excessive blood or smoke are detected in a surgical scene, the first algorithm, i.e., deep learning algorithm, that has been trained on images exhibiting presence of blood and smoke. These conditions may be detected by separate image processing means that trigger the presence of blood and smoke in the scene. These image processing triggers may be further verified by inputs from the control software based on activations of cutting and energy tools.

In one of the embodiments, at step 200, a pixel-wise mask for the areas of low local visual information is generated. A further morphological dilation step 202 may be employed to extend the mask representing these areas of low local visual information. The first algorithm is used to generate the depth estimation for these low local visual information regions at step 204, where the integration of global context is more important. The second algorithm is then used at step 206 to generate depth estimation for the remaining pixels in the image where high local visual information is observed.

In the embodiments where a classical algorithm is used as one of the two algorithms, plurality of pixels labeled as 'inconsistent pixels' are routinely observed as output by the classical algorithm. A classical algorithm, working in the local pixel neighborhood, marks the pixels that cannot be reliably matched between the left and right stereo image as "inconsistent pixels." An exemplary scenario where large patches of inconsistent pixels appears is the case of large low contrast areas in the surgical scene. The areas of surgical scene that are larger than the disparity comparison block size of the classical algorithm with no high-contrast spots or unique edges in the region often get marked as belonging to inconsistent pixels. A possible solution to this problem may use semi-global block matching' (SGBM) algorithms. However, the classical methods from the SGBM family of algorithms increase the processing cost by a factor of 10× to 20× and still suffer from this problem in the case of large low contrast areas with gradual depth changes. In these embodiments, the absent depth values of inconsistent pixels, from the classical algorithm, may be filled in with the depth estimation values from the first algorithm, where the first algorithm is able to combine global context and to compute correct depth estimate in the large areas of low contrast.

The classical and machine learning algorithms of the present disclosure are configured to generate distinct disparity maps. The video processing device 56 may then combine these disparity maps to generate the final consistent disparity map and depth estimation image. The final disparity map may be represented as a point cloud showing the depth value for each pixel. A desirable application for this depth information may be used to display 3D visual information on a 2D screen such as the second display 34. In further embodiments, a pre-operative imaging model registered with intra-operative stereo endoscope image may also be displayed on the second display 34. Since a colorless and texture-less point cloud shown on the second display 34 fails to convey visually coherent information from surgical scene in a way that is instantaneously useful to the surgeon intra-operatively, the final disparity map may be used to provide color/texture for each pixel in the point cloud generated from this method. The color/texture value for each pixel may be a combination of the color/texture values according to the first algorithm and the second algorithm.

In some surgical procedures, an initial phase commonly known as "first look", may be employed wherein the surgeon moves the endoscopic camera 51 around the surgical scene to get a better understanding of the patient-specific internal anatomy and plan a route to the organ for surgery. During this phase, the stereo endoscopic camera 51 is moved and panned around to get a better look at the surgical site. The main challenge for the stereo algorithms to reliably infer depth estimation during this phase is excessive motion artifacts caused by motion blur.

Figure 10:
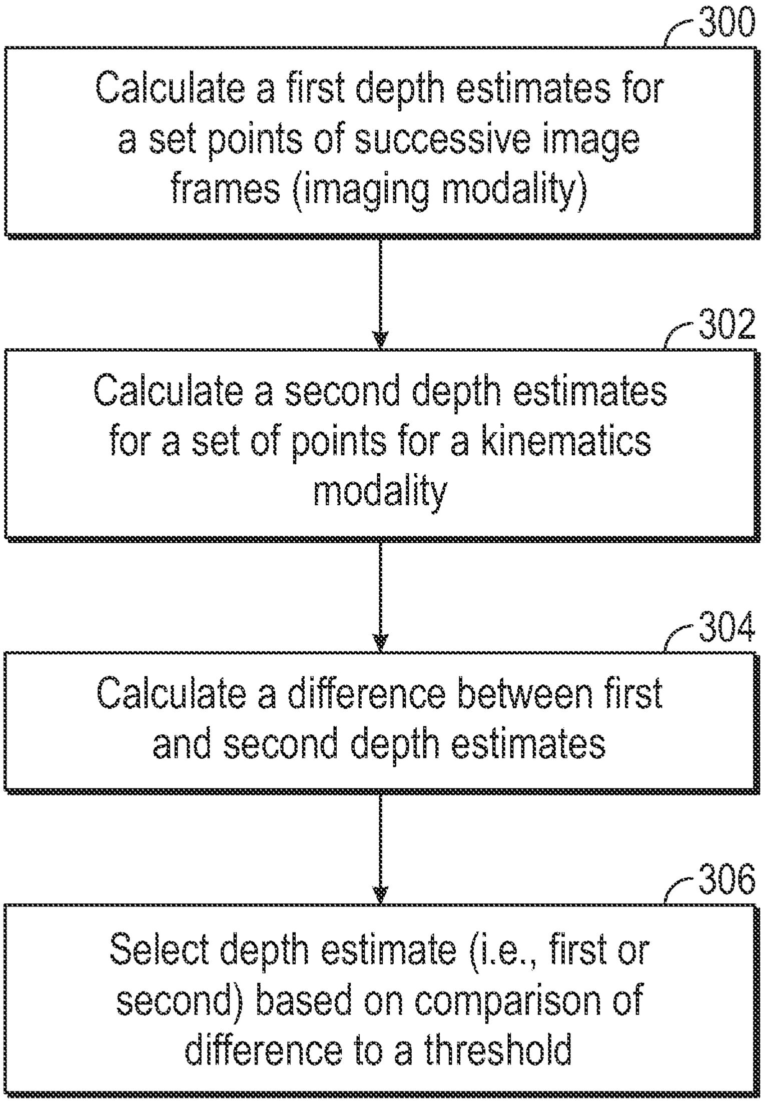
FIG. 10 is a flow chart of a method for depth estimation in blurry images according to an embodiment of the present disclosure.

In one embodiment of this disclosure, a method for depth estimation in blurry images due to motion artifacts is shown in FIG. 10. Presence of excessive motion blur is detected through kinematics (e.g., user input commands, movement of the robotic arm 40) or through image processing to detect visual cues. In particular, the video processing device 56 may compute the relative motion between successive frames based on kinematics. Once this motion blur mode is detected, the video processing device 56 selects a depth estimation algorithm that is more robust to motion blur is executed to perform depth mapping.

At step 300, a first depth estimates for a set of points between successive frames is calculated by the video processing device 56 using the best algorithm for depth estimation. This depth estimate from multiple key-points from successive images is combined to generate a first global change in depth estimate from successive image frames. At step 302, a second global depth estimates from kinematics is computed with a suitable sampling rate aligned with video frame acquisition rate. At step 304, a difference between the first global change in depth estimate from imaging modality and the second global depth estimate from kinematics modality is computed. The difference is then compared to a threshold. If the difference between the first global change in depth estimate from imaging modality and the second global change in depth estimate from kinematics modality is larger than a threshold, then at step 306 the video processing device 56 switches over to the depth estimation estimate that is more suitable to scenes with excessive motion. The video processing device 56 uses the estimate of inter-frame endoscope movement based on kinematics or other means to select the most suitable depth estimation algorithm is being used.

The present disclosure also provides for tissue specific modeling (liver, stomach, lung, etc.) based on temporal conditions and imposing explicit model-based constraints in domain specific depth mapping applications. Due to basic physiologic constraints, there is a high degree of similarity in the structure of the surgical field observed from multiple patients undergoing the same surgical procedure. In the surgical domain, bio-mechanical models, designed through analytical and data driven techniques, may be used to inform and improve depth maps created from both classical and machine learning modules. For example, stereo endoscope views of soft tissue scenes often contain extreme saturation, specular reflection, and numerous other confounding factors that prevent reliable depth estimates. Human organs are often homogeneous in texture and appearance, especially when viewed at the coarser scale associated with the wider field of view used for early-stage surgical planning. In combination, these factors can make accurate depth estimation challenging. Use of explicit bio-mechanical models allows accumulation of both local and global cues when creating a final depth map. A deformable bio-mechanical organ model may be used to address deficiencies in an initial depth map. Thus, if the initial depth map is sparse and/or noisy, the estimated intraoperative surface may contain enough unique structure to drive a deformable organ registration step. After alignment, the surface of the aligned organ may be used to refine and complete the initial depth map, using various strategies.

Machine learning models with a complex representational capacity, such as deep learning models, could potentially learn a similar implicit bio-mechanical constraint if provided with enough diverse and domain specific data, however, there are several advantages to using an explicit model. While it may be possible to learn an implicit model "inside" a CNN (i.e., in latent space), it will most likely be data limited and difficult to control or tune. In the case of real training data, it may be challenging to acquire enough samples. Synthetic images may be used to generate larger and more diverse datasets containing more variations in organ pose, but this path will likely introduce some degree of "unrealism" that may hinder generalization of the learned model itself. An explicit model may be designed and verified independently (e.g., through finite element methods) and combined with one or more independent depth estimation modules through a real time fusion strategy. Thus, any of the disclosed depth mapping methods may be based on organ tissue specific models.

To a large extent, the quality of depth maps resulting from stereo reconstruction modules is directly proportional to the quality of the input images. In addition to all the common attributes of typical high quality monocular images (e.g., focus, uniform illumination, etc.), stereo image pairs must contain unique visual structure (or features) in both left and right images, since it is this common structure that is exploited to determine the pixelwise correspondence that is encoded in the output disparity maps. If this common structure is not visible, then stereo reconstruction processing will suffer. In human tissue, different structures are revealed by different wavelengths of light. For example, visible wavelengths will primarily reveal surface structure, whereas near-infrared wavelengths may reveal slightly deeper structures.

Near infrared (NIR) techniques can therefore produce images that are complementary to standard visible wavelength imaging. In cases where tissue surface is homogeneous in visible wavelength imaging, resulting in poor stereo reconstructions, near-infrared sensors may reveal sufficient common structure (e.g., subdermal micro-vasculature) to improve depth maps in these scenarios. This information can be combined in both late-stage fusion (i.e., wavelength specific depth maps) and early-stage fusion (i.e., multi-spectral input images) strategies. In some cases, depth maps resulting from NIR imaging, may deviate slightly from the true surface, and fusion strategies can use prior physiologic knowledge to account for this. Thus, one the image processing algorithms used in the methods of the present disclosure may also include NIR light and image sources, such that in addition to the visible spectrum depth maps, depth maps may also be computed from NIR images to supplement or verify depth maps generated using machine learning and/or classical algorithms using visible spectrum depth maps.

In addition, to NIR imaging, other lighting and illumination may be used to enhance depth mapping. Spot and/or gradient or colored lighting may be used to enhance contours of the tissue surfaces. If illumination spot is not showing up in the proper location, then a second algorithm may be used to confirm/verify the mismatch. Since the location of the light source is known, the position may then be used to triangulate distances to orthogonal tissue surfaces. Illumination spot causes specular reflection on tissue surface closer to the endoscope with surface normal in the direction of the endoscope camera, which may be used in depth mapping.

Figure 11:
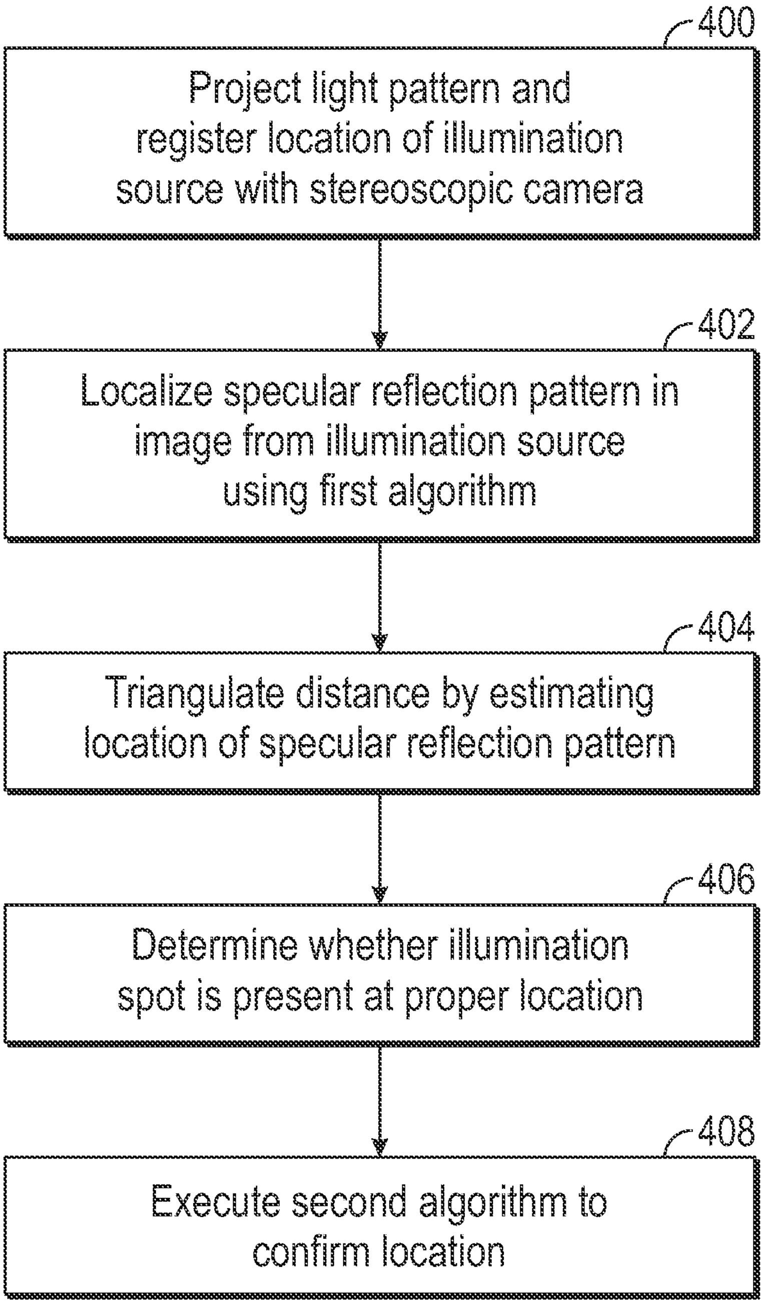
FIG. 11 is a flow chart of a method for stereoscopic calibration of the stereoscopic endoscopic system for according to an embodiment of the present disclosure.

The system 10 may use endoscope instrument interface, i.e., communication between the controller 21*a* and the video processing device 56, to query in real-time the illumination level. The illumination level determines the amount of specular reflection to be expected in the image. With reference to FIG. 11, a method for stereo calibration of the stereo endoscopic system (i.e., the video processing device 56 and the endoscopic camera 51) includes outputting a projected pattern and registering the physical location of the illumination source with respect to the two cameras in the endoscopic camera 51 at step 400. Using the stereoscopic calibration parameters (e.g., intrinsic and extrinsic parameters for each camera, such as focal lengths, baseline, etc.) along with the registered location of illumination with respect to the stereo baseline, the video processing device 56 then uses the epipolar geometry constraints to localize the specular reflection pattern, e.g., spot or gradient, in each image at step 402 using a first image processing algorithm. Furthermore, the video processing device 56 then triangulates distances to orthogonal tissue surfaces by estimating the location of specular reflection spot in each of the two images at step 404. At step 406, the video processing device 56 determines whether the illumination spot is present in the proper location. If not, then at step 408, a second image processing algorithm is executed to confirm/verify location of the illumination spot. If neither algorithm is capable of identifying the projected pattern, then a prompt is made that calibration failed. If spot is detected, then a prompt is output that calibration is successful.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:

an endoscopic camera configured to output a stereoscopic video stream;

a video processing unit coupled to the endoscopic camera, the video processing unit configured to:

process the stereoscopic video stream using a first image processing algorithm comprising a deep learning image processing algorithm to obtain a first depth map;

process the stereoscopic video stream using a second image processing algorithm comprising an analytical reconstruction algorithm to obtain a second depth map, wherein the first image processing algorithm and the second image processing algorithm process the same stereoscopic video stream;

compare corresponding depth values of the first depth map and the second depth map to determine a degree of agreement between the first depth map and the second depth map;

determine, based on the degree of agreement, whether the first depth map is accurate; and display the stereoscopic video stream enhanced by the first depth map depending on whether the first depth map is accurate.

2. The surgical robotic system according to claim 1, wherein the deep learning image processing algorithm is adjusted based on the second depth map.

3. The surgical robotic system according to claim 1, further comprising:

a robotic arm including an instrument and at least one torque sensor.

4. The surgical robotic system according to claim 3, wherein the second image processing algorithm receives sensor feedback corresponding to physical contact by the instrument from the at least one torque sensor.

5. A method for processing video data of a surgical scene, the method comprising:

outputting a stereoscopic video stream from an endoscopic camera to a video processing unit;

processing the stereoscopic video stream using a first image processing algorithm comprising a deep learning image processing algorithm to obtain a first depth map;

processing the stereoscopic video stream using a second image processing algorithm comprising an analytical reconstruction algorithm to obtain a second depth map, wherein the first image processing algorithm and the second image processing algorithm process the same stereoscopic video stream;

comparing corresponding depth values of the first depth map and the second depth map to determine a degree of agreement between the first depth map and the second depth map;

determining, based on the degree of agreement, whether the first depth map is accurate; and displaying the stereoscopic video stream enhanced by the first depth map depending on whether the first depth map is accurate.

6. The method according to claim 5, further comprising:

generating a virtual wall based on the first depth map; and limiting movement of a robotic arm based on the virtual wall.

7. The method according to claim 5, adjusting the deep learning image processing algorithm based on the second depth map.

8. The method according to claim 7, wherein processing the stereoscopic video stream using the second image processing algorithm, further includes receiving sensor feedback from at least one torque sensor corresponding to physical contact by a robotic instrument.

* * * * *